United States Patent
Morningstar

(10) Patent No.: US 8,491,621 B2
(45) Date of Patent: Jul. 23, 2013

(54) INSTRUMENT WITH EXPANDABLE MEMBER CONFIGURED TO PREPARE A PENIS FOR IMPLANTATION OF A PENILE PROSTHETIC

(75) Inventor: Randy L. Morningstar, Brooklyn Park, MN (US)

(73) Assignee: Coloplast A/S, Humlebaek (DK)

( * ) Notice: Subject to any disclaimer, the term of this patent is extended or adjusted under 35 U.S.C. 154(b) by 181 days.

(21) Appl. No.: 12/877,113

(22) Filed: Sep. 8, 2010

(65) Prior Publication Data

US 2011/0166590 A1 Jul. 7, 2011

(51) Int. Cl.
*A61M 29/00* (2006.01)

(52) U.S. Cl.
USPC ...................... 606/192; 604/99.04

(58) Field of Classification Search
USPC ............ 606/190–199; 600/38–41; 604/96.01, 604/97.01–97.03, 98.01–98.02, 99.01–99.04, 604/103, 103.01–103.04, 103.11, 104–109, 604/101.03; 128/897–899; 623/11.11
See application file for complete search history.

(56) References Cited

U.S. PATENT DOCUMENTS

| | | | |
|---|---|---|---|
| 4,244,370 A | 1/1981 | Furlow et al. | |
| 4,350,151 A | 9/1982 | Scott | |
| 4,396,021 A | 8/1983 | Baumgartner | |
| 4,622,958 A | 11/1986 | Finney | |
| 5,458,612 A * | 10/1995 | Chin | 606/192 |
| 5,588,965 A | 12/1996 | Burton et al. | |
| 5,868,729 A | 2/1999 | Pelfrey | |
| 6,102,929 A | 8/2000 | Conway et al. | |
| 2002/0055756 A1* | 5/2002 | Thornton | 606/190 |
| 2002/0198558 A1* | 12/2002 | Briscoe et al. | 606/192 |
| 2004/0097997 A1* | 5/2004 | Di Cecco | 606/162 |
| 2004/0220522 A1* | 11/2004 | Briscoe et al. | 604/99.04 |
| 2012/0330344 A1* | 12/2012 | Tutav et al. | 606/196 |

FOREIGN PATENT DOCUMENTS

| | | |
|---|---|---|
| WO | 95/03848 | 2/1995 |
| WO | 03071970 A1 | 9/2003 |

* cited by examiner

*Primary Examiner* — Gary Jackson
*Assistant Examiner* — Katrina Stransky
(74) *Attorney, Agent, or Firm* — Coloplast Corp., Coloplast A/S; Nick Baumann

(57) ABSTRACT

An instrument configured to prepare a penis for implantation of a penile prosthetic includes a rigid shaft extending between a proximal end and a distal end that is insertable into the penis, and an expandable member coupled to a distal end portion of the shaft. The expandable member is movable between a first position having a first diameter that is substantially equal to a diameter of the rigid shaft and a second position having a second diameter that is larger than the diameter of the rigid shaft and configured to dilate tissue of the penis.

13 Claims, 7 Drawing Sheets

INSTRUMENT WITH EXPANDABLE MEMBER CONFIGURED TO PREPARE A PENIS FOR IMPLANTATION OF A PENILE PROSTHETIC

BACKGROUND

Implanted penile prostheses address erectile dysfunction in men.

In a typical implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Thereafter, a tool (e.g., a "Furlow" introducer) is inserted into each corpora cavernosum to measure a length of the penis distally and proximally from a "stay" suture or other stationary landmark located near the opening formed in the fascia. Subsequently, each corpora cavernosum is dilated with at least one separate dilation tool, and often multiple dilation tools. For example, each corpora cavernosum is dilated by introducing gradually larger stainless steel rods into the corpora cavernosum to form a recess in the penis that is sized to receive a cylinder of the penile prosthesis.

The above-described procedure has proven effective in the implantation of penile prostheses. However, practitioners have expressed a continuing desire for more efficient and cost effective tools and procedures for implanting penile prostheses.

SUMMARY

One aspect provides an instrument configured to prepare a penis for implantation of a penile prosthetic. The instrument includes a rigid shaft extending between a proximal end and a distal end that is insertable into the penis, and an expandable member coupled to a distal end portion of the shaft. The expandable member is movable between a first position having a first diameter that is substantially equal to a diameter of the rigid shaft and a second position having a second diameter that is larger than the diameter of the rigid shaft and configured to dilate tissue of the penis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
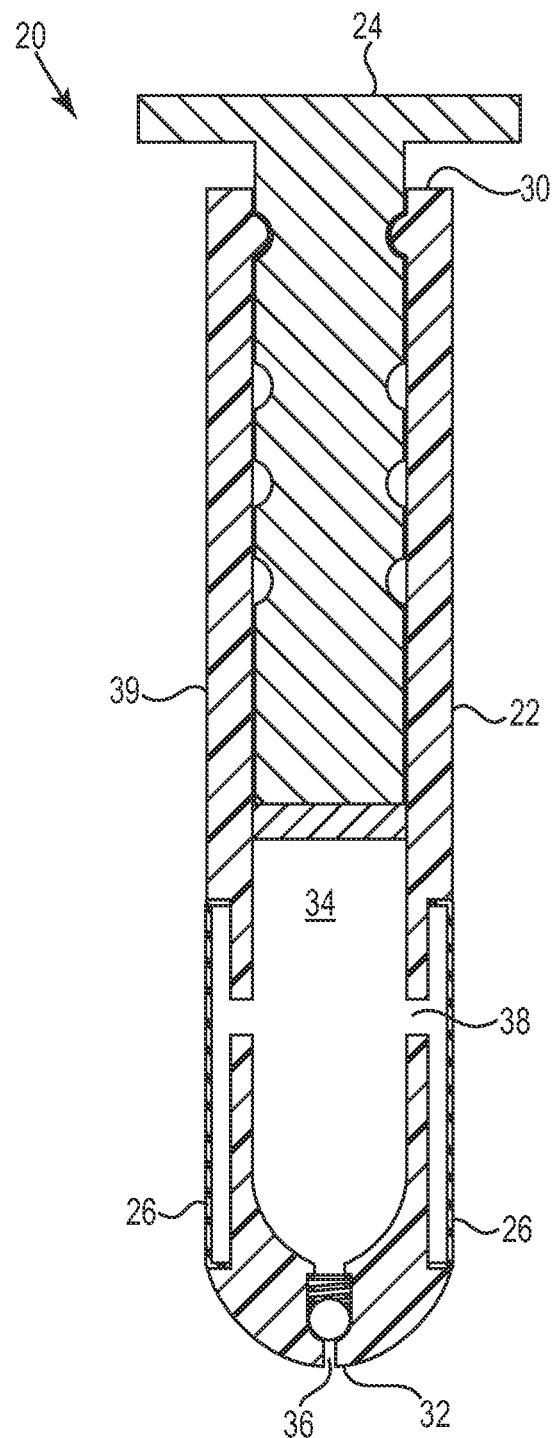
FIG. 1 is a cross-sectional view of one embodiment of an instrument configured to prepare a penis for implantation of a penile prosthetic.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

Multiple different tools and instruments are employed in a typical penile prosthetic implantation procedure to form a recess sized to receive the implant. In general, the fewer tools employed during a body implant procedure, the better.

Embodiments provide an instrument that is configured to prepare a penis for implantation of a penile prosthetic, where the instrument includes a first state characterized by a substantially uniform shaft diameter that is suited for measuring a length of a corpora cavernosa of the patient, and an expandable member that is configured to rigidly expand in a lateral direction from the shaft dilate corpora cavernosa of the patient. The expandable member, when expanded/dilated, is suited to core and displace tissue in the corpora cavernosa of the penis. The instrument thus provides a combination measurement and dilation tool that offers dilation of the corpora with improved procedural efficiency, which obviates the use of multiple different tools during the implantation of a penile prosthetic to provide additional surgical efficiencies.

FIG. 1 is a cross-sectional view of one embodiment of an instrument 20 configured to prepare a penis for implantation of a penile prosthetic. The instrument 20 includes a shaft 22, a plunger 24 that is movably inserted into the shaft 22, and an expandable member 26 coupled to the shaft 22.

The shaft 22 extends between a proximal end 30 and a distal end 32. In one embodiment, the shaft 22 includes a fluid chamber 34 formed within the shaft 22, an orifice 36 formed in the distal end 32 that communicates with the fluid chamber 34, and a fluid pathway 38 that is formed in the shaft to communicate between the fluid chamber 34 and expandable member 26. The plunger 24 is movable within the shaft 22 to aspirate/draw liquid into the fluid chamber 34, and once the fluid chamber 34 is charged with liquid, the plunger 24 is movable to expand the expandable member 26 to a wider dilation configuration.

Figure 4A:
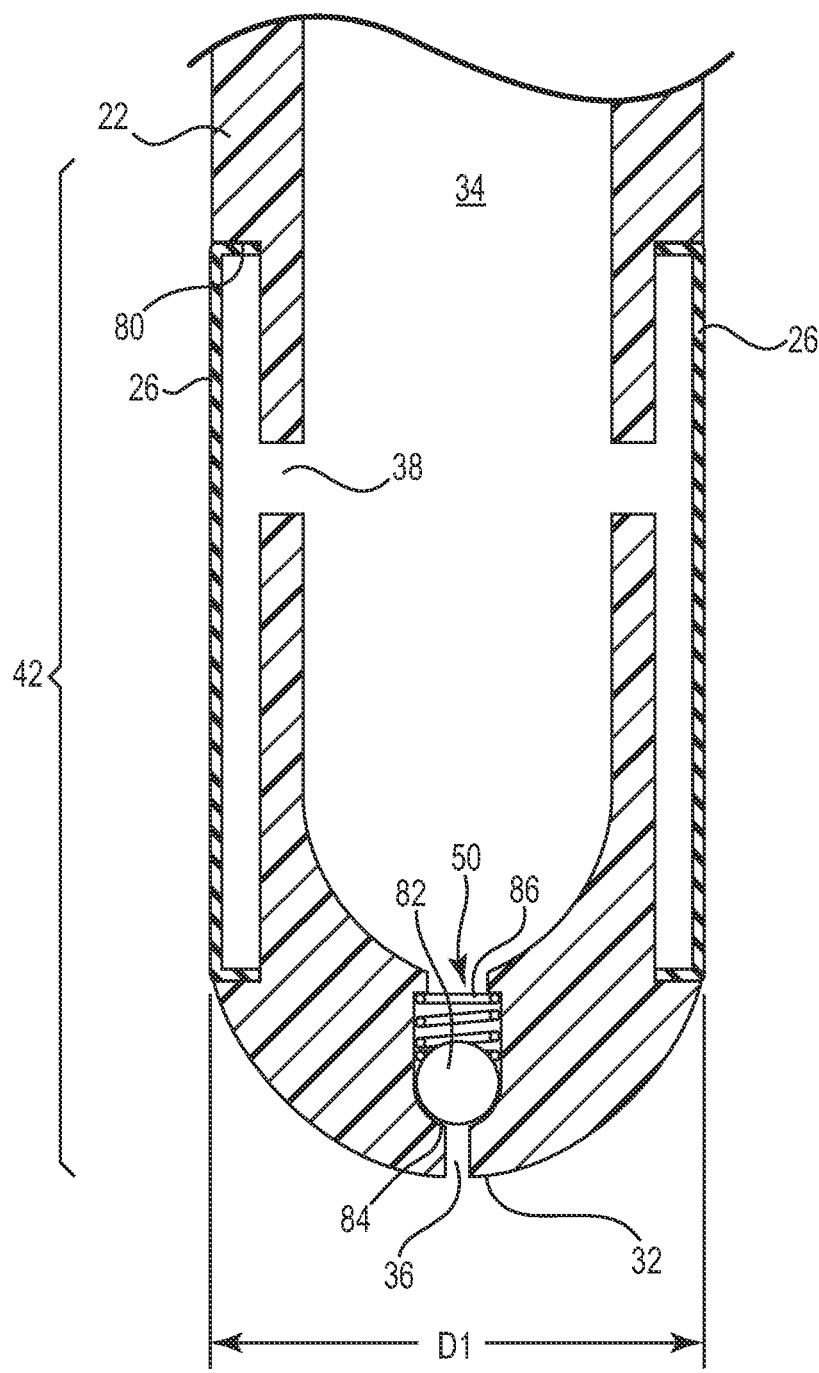
FIG. 4A is a cross-sectional view of a distal end portion of the instrument illustrated in FIG. 1.
Figure 4B:
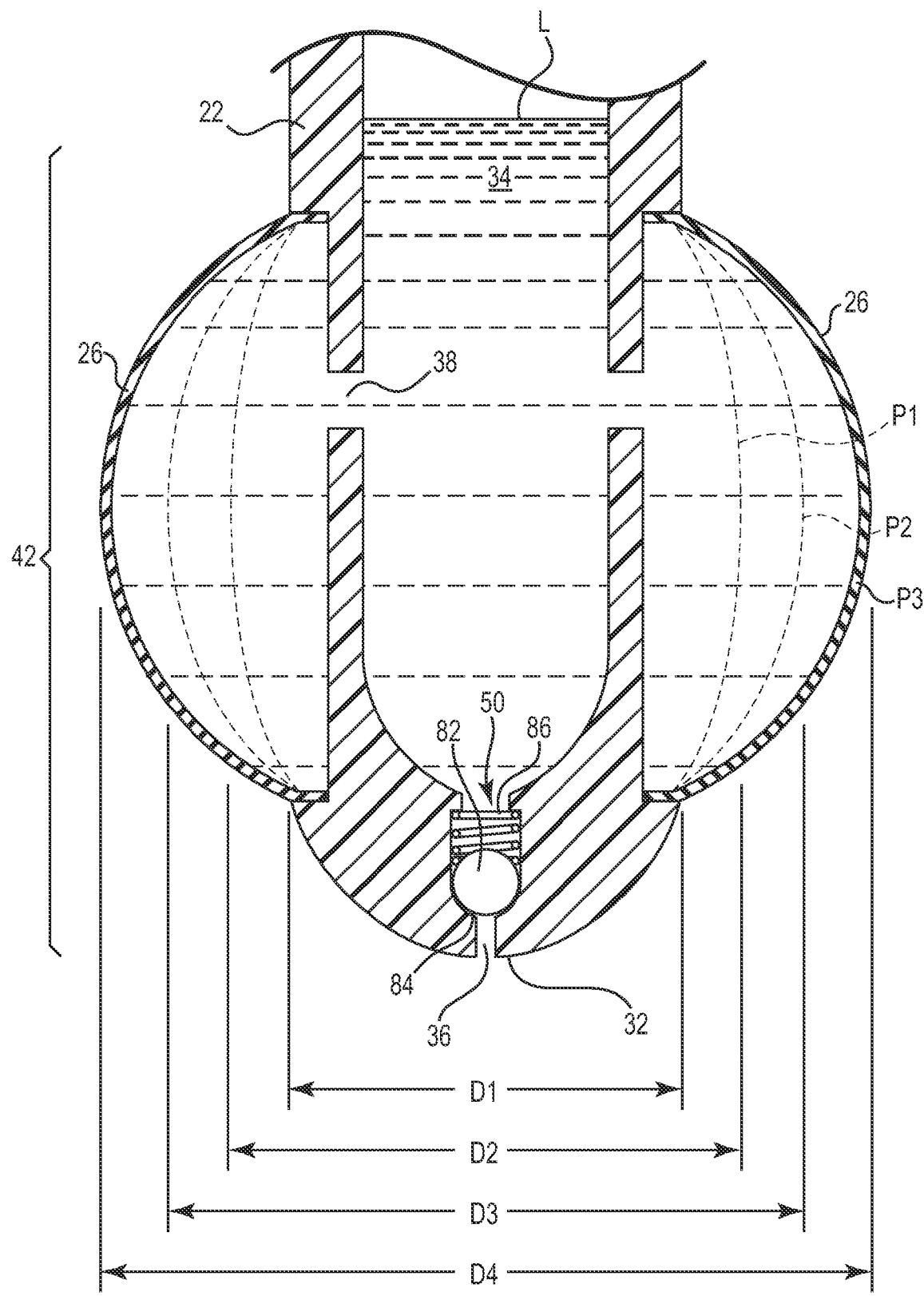
FIG. 4B is a cross-sectional view of the distal end portion of the instrument illustrated in FIG. 1 showing three different controlled expansion configurations for an expandable dilation member of the instrument.

The expandable member 26 thus is movable between a deflated state (as shown) and an inflated state (FIG. 4B). When the expandable member 26 is in the deflated state, the instrument 20 has a substantially uniform and uninterrupted diameter that is suited for insertion into the corpora cavernosa for measuring a length of each corpora cavernosum of the penis. In one embodiment, an exterior surface of the shaft 22 includes measurement markings 39 that allow the user to measure the length of each corpora cavernosa in centimeters. In one embodiment, the markings 39 extend from zero centimeters at the distal end 32 of the shaft to approximately 20 centimeters behind the distal end 32, although other ranges for the length measurement and other units of measure are also acceptable.

The plunger 24 is movable to inflate the expandable member 26 laterally away from the shaft 22, which places the expandable member 26 in the inflated state useful for dilating a diameter of each corpora cavernosum of the penis. The instrument 20 allows the approach of first measuring the length of the corpora with the marking 39 on the shaft 22 as inserted into the corpora, and then expanding the expandable member 26 to dilate the corpora while the shaft 22 is inside the corpora. The instrument 20 provides stops for the plunger 24 as it moves into the shaft 22 and the fluid chamber 34, as described below, to allow the controlled and selective expansion (e.g., dilation width) of the expandable member 26.

Figure 2:
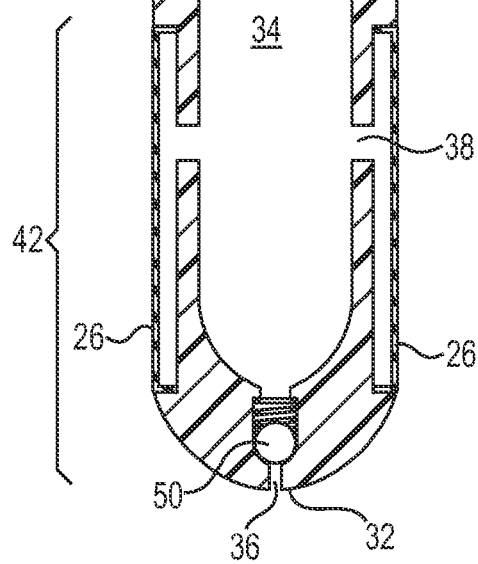
FIG. 2 is a cross-sectional view of a shaft of the instrument illustrated in FIG. 1.

FIG. 2 is a cross-sectional view of one embodiment of the shaft 22. The shaft 22 includes a proximal end portion 40 that extends from the proximal end 30 and a distal end portion 42 that extends from the distal end 32. In one embodiment, the fluid chamber 34 is an axial bore formed in the shaft 22 and communicates with the orifice 36 formed in the distal end 32 and with the expandable member 26 via the fluid pathway 38.

The expandable member 26 is generally coupled to the distal end portion 42 of the shaft 22. In one embodiment, the expandable member 26 is a film that is sealed to at least a portion of an exterior side surface of the shaft 22, where the film is expandable to provide a bulb or dilation balloon. In one embodiment, the expandable member 26 is sealed around the entire periphery of the shaft 22.

In one embodiment, the fluid pathway 38 is formed in the distal end portion 42 of the shaft 22 as one opening, or as a series of holes. In one embodiment, the fluid pathway 38 is formed in the distal end portion 42 of the shaft 22 as a slot section or a series of slot sections. While not visible in the cross-sectional view of FIG. 2, portions of the sidewall of the shaft 22 extend between the proximal and distal end portions 40, 42 to provide the shaft 22 with structural rigidity along its length.

In one embodiment, a check valve 50 is provided in the distal end portion 42 of the shaft proximal the orifice 36. The check valve 50 is configured to open to allow the orifice 36 to draw liquid into the fluid chamber 34 and to close to prevent the liquid within the fluid chamber 34 from exiting the shaft 22 through the orifice 36. The check valve 50, when closed, functions to force the liquid as it is pressurized within the fluid chamber 34 by the plunger 24 to flow through the fluid pathway 38, which expands the expandable member 26.

In one embodiment, one or more detents 52 are formed on an interior surface 54 of the shaft 22. The detents 52 cooperate with the plunger 24 (FIG. 1) to provide for the controlled and selective pressurization of the fluid within the fluid chamber 34.

Figure 3:
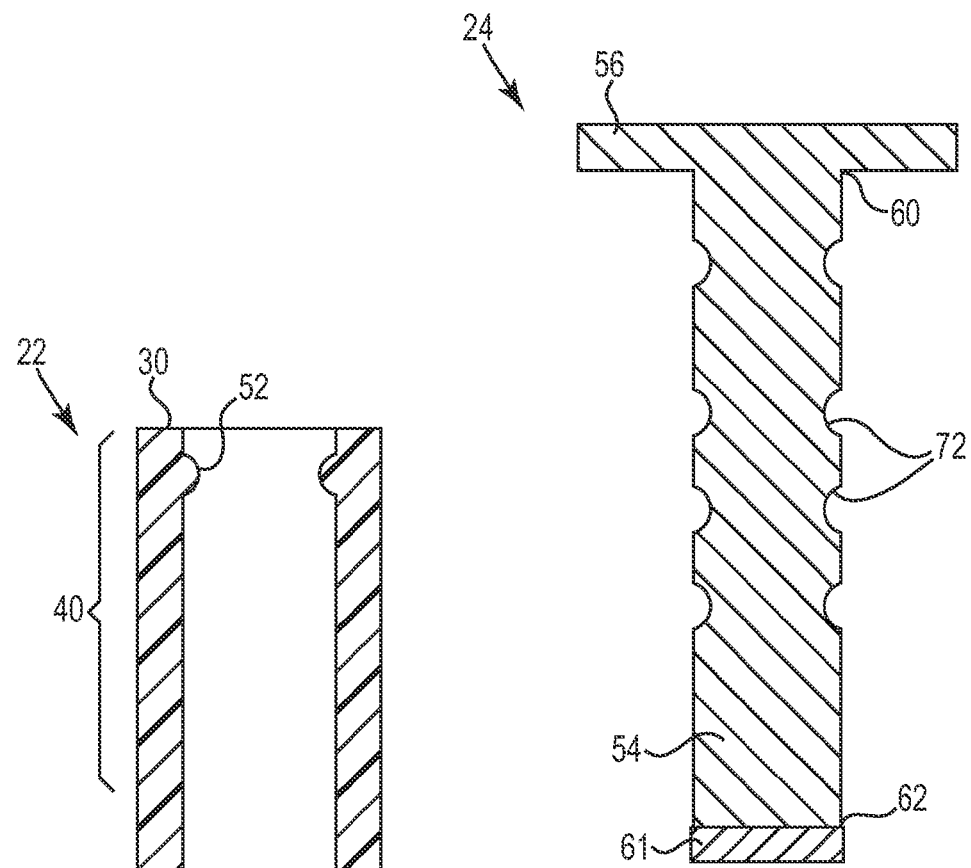
FIG. 3 is a side view of a plunger of the instrument illustrated in FIG. 1.

FIG. 3 is a cross-sectional view of the plunger 24. The plunger 24 includes a rod 54, a handle 56 attached to a proximal end of 60 of the rod 54, and a seal 61 attached to a distal end 62 of rod 54. The rod 54, the handle 56, and the seal 61 may be formed as a unitary monolithic piece, for example via molding, or these components may be provided separately and attached during fabrication. As an example, the rod 54 and the handle 56 are suitably molded from polysulfone around a ring of softer polymer (e.g., silicone) that forms the seal 61.

In one embodiment, handle 56 is provided as a flange or as a pair of opposing wings or other appendages that extend beyond the rod 54. The flange allows the palm of the surgeon to press the plunger 24 into the shaft 22 (FIG. 2) and also provides a surface that allows the plunger 24 to be withdrawn from the shaft 22 by, for example, the index and middle finger of the surgeon.

In one embodiment, the rod 54 is formed to include a series of stop detents 72 extending between the proximal end 60 and the distal and 62. With additional reference to FIG. 2, the stop detents 72 cooperate with the detents 52 formed in the shaft 22 to allow the plunger 24 to be pressed into the shaft 22 at controlled, incremental intervals to selectively pressurize the fluid within the fluid chamber 34. For example, engaging the first stop detents 72 adjacent to the distal end 62 with the detents 52 of the shaft 22 will pressurize the liquid in the fluid chamber 34 to a first pressure. Pressing the plunger 24 an additional distance into the shaft 22, for example such that the stop detents 72 adjacent to the proximal end 60 engage with the detents 52, will pressurize the liquid in the fluid chamber 34 to a second pressure that is greater than the first pressure. The expandable member 26 is configured to respond to the pressure of the liquid within the fluid chamber 34 such that the expandable member 26 expands laterally away from the shaft 22 as a function of the increase in the pressure of the liquid inside the fluid chamber 34, as illustrated in FIG. 4B.

In one embodiment, the stop detents 72 are formed as annular grooves around the rod 54. In one embodiment, the stop detents 72 are formed as helical grooves that are provided to enable the plunger 24 to be "screwed" into the detents 52 of the shaft 22.

In one embodiment, the instrument 20 is configured to be reusable and is fabricated from a suitable material such as a polymer or a metal. Suitable materials for the shaft 22 and the plunger 24 include polysulfone, polyetherimide, polyester or blend or derivatives of polyester. One suitable material for the expandable member 26 is a thin sheet or film of polyester that is expandable when pressurized by liquid in the fluid chamber 34. In one embodiment, the shaft 22 and the plunger 24 are each fabricated from polysulfone and the balloon 26 is formed of a polyester film, which configures the instrument 20 for disposable single surgical use.

FIG. 4A is a cross-sectional view of the distal end portion 42 of the shaft 22. The shaft 22 has a uniform outside shaft diameter D1 when the expandable member 26 is in the unexpanded state. In one embodiment, a recessed shoulder 80 is formed in the shaft 22 to receive opposing edges of the expandable member 26. That is to say, the recessed shoulder 80 provides the distal end portion 42 of the shaft 22 with a recessed section, where the recessed section is recessed relative to the diameter D1 of the proximal end portion 40 (FIG. 2) of shaft 22. The expandable member 26 is disposed in the recessed section such that when the expandable member 26 is at rest (or deflated) the distal end portion 42 of the shaft 22 has a cross-sectional corresponding with the diameter D1. Thus, in one embodiment the instrument 20 is provided with a substantially uniform diameter between the proximal end portion 40 and the distal end portion 42 of the shaft 22.

In one embodiment, the expandable member 26 is provided as a polyester film and is sealed around a periphery of the distal end portion 42 of the shaft 22. The polyester film of the expandable member 26 is configured to balloon out when expanded and have sufficient rigidity to allow the instrument 20 to dilate the corpus spongiosum tissue within each corpora cavernosa.

The check valve 50 is disposed in the distal end portion 42 of the shaft 22 proximal the distal end 32. In one embodiment, the check valve 50 is a one-way ball valve having a ball 82 that is biased against a surface 84 by a spring assembly 86. The one-way ball valve 50 is configured to allow liquid to be drawn from outside the shaft 22, through the orifice 36, past the biased ball 82, and into the fluid chamber 34. When the liquid in the fluid chamber 34 is pressurized, the spring assembly 86 forces the ball 82 to seat against the surface 84 and prevents the liquid from exiting the shaft 22 through the orifice 36. As a consequence, the pressurized liquid flows through the fluid pathway 38 and exerts a force on the expandable member 26.

In one embodiment, the check valve 50 is located proximal to the entrance to the orifice 36 to allow the distal end 32 of the instrument 20 to be dipped "leading end first" into a container of liquid to allow for the subsequent aspiration of liquid into the fluid chamber 34. Thus, the liquid loading port for the instrument 20 is located at the leading end, which is the distal-most end 32 of the shaft 22.

FIG. 4B is a schematic view of the distal end portion 42 of the instrument 20 illustrating activation of the expandable member 26. The fluid chamber 34 has been charged with liquid L or "primed," for example by retracting the plunger 24 in the proximal direction out of the shaft 22 (FIG. 1). The expandable member 26 expands laterally away from the shaft 22 as a function of the increase in the pressure of the liquid L inside the fluid chamber 34 as the plunger 24 is pressed distally into the shaft 22.

Instrument 20 is configured to measure the corpora by providing a substantially uniform diameter D1 when the expandable member 26 is deflated (e.g., when the pressure inside the fluid chamber 34 is balanced with the pressure outside of the fluid chamber 34, which is denoted herein as a pressure condition of P0). The expandable member 26 expands laterally away from the shaft 22 as the pressure in the liquid L within the fluid chamber 34 is increased, which configures the instrument 20 for selective and controlled dilation of the corpora.

For example, at a first increased pressure of P1, the expandable member 26 expands laterally away from the shaft 22 to provide a dilation diameter of D2 for the instrument 20. The expandable member 26 expands laterally away from the shaft 22 to a dilation diameter of D3 when the pressure is increased to a pressure of P2. The expandable member 26 expands laterally away from the shaft 22 to a dilation diameter of D4 when the pressure is increased to a pressure of P3. In one embodiment, the expandable member 26 is expanded laterally away from the shaft 22 in a controlled manner such that the expandable member 26 is maintained at the dilation diameter of D2 associated with pressure P1. In one embodiment, the expandable member 26 is expanded laterally away from the shaft 22 in controlled increments, for example from the dilation diameter of D2 associated with pressure P1 to the dilation diameter of D3 associated with the pressure of P2 and then maintained at the dilation diameter of D3.

The diameter size range between the diameters D1-D4 is selected based upon the end use or desired end result. The diameter size range between the diameters D1-D4 in one exemplary embodiment ranges from 2 mm to 20 mm or more. In one embodiment, the diameter D1 is 8 mm, the diameter D2 is 10 mm, the diameter D3 is 12 mm, and the diameter D4 is 14 mm. Thus, one embodiment of the instrument 20 includes an expandable member 26 that is inflatable from the first diameter D1 to a second diameter D2 that is larger than the diameter D1, where the second diameter D2 a ranges between 100-200% of D1.

In one exemplary embodiment, the expandable member 26 is coupled to the distal end portion 42 of the shaft 22 and is movable between a first position as illustrated in FIG. 4A having a first diameter D1 that is substantially equal to a diameter of the rigid shaft 22 and a second position (for example, as shown by P2 in FIG. 4B) having a second diameter D3 that is larger than the diameter D1 of the rigid shaft 22 and is thus so configured to dilate tissue in the corpora of the penis.

Figure 5A:
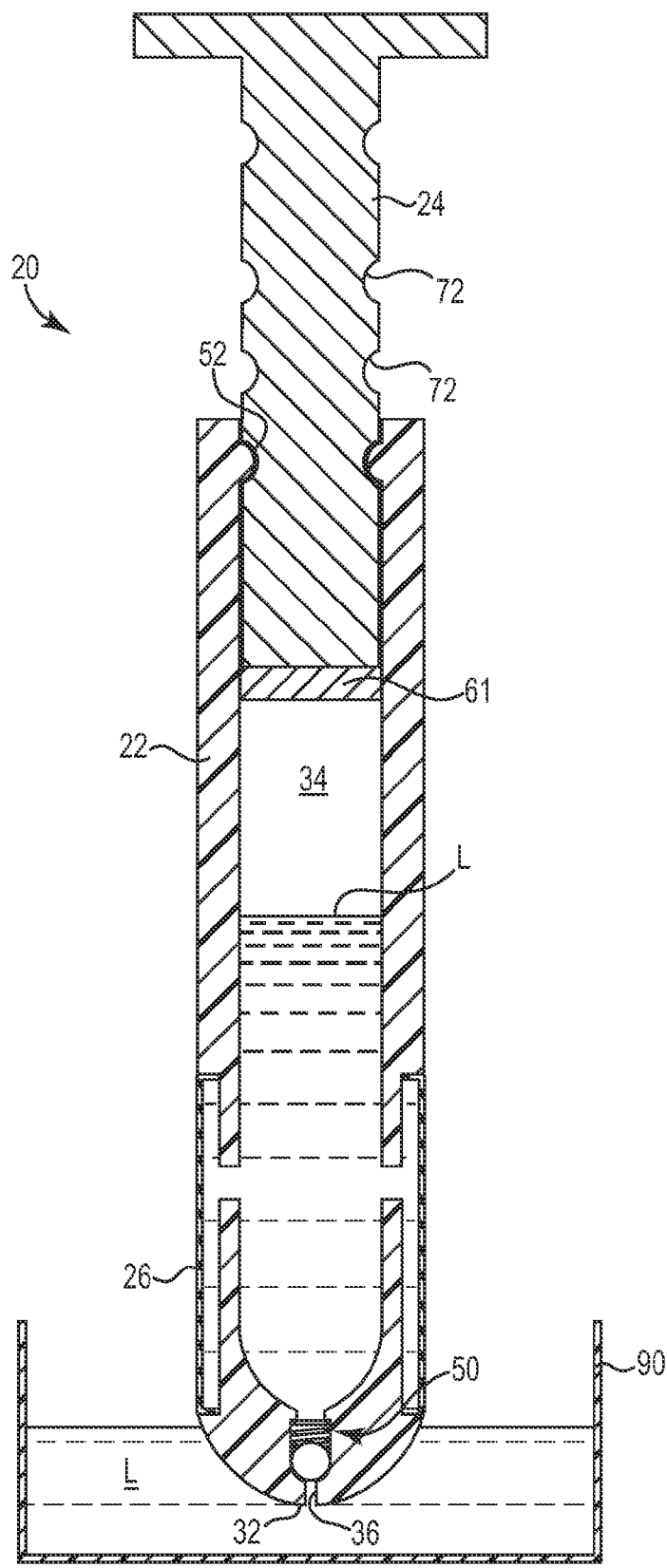
FIG. 5A is a cross-sectional view of the instrument illustrated in FIG. 1 primed by aspirating liquid into an internal fluid chamber according to one embodiment.
Figure 5B:
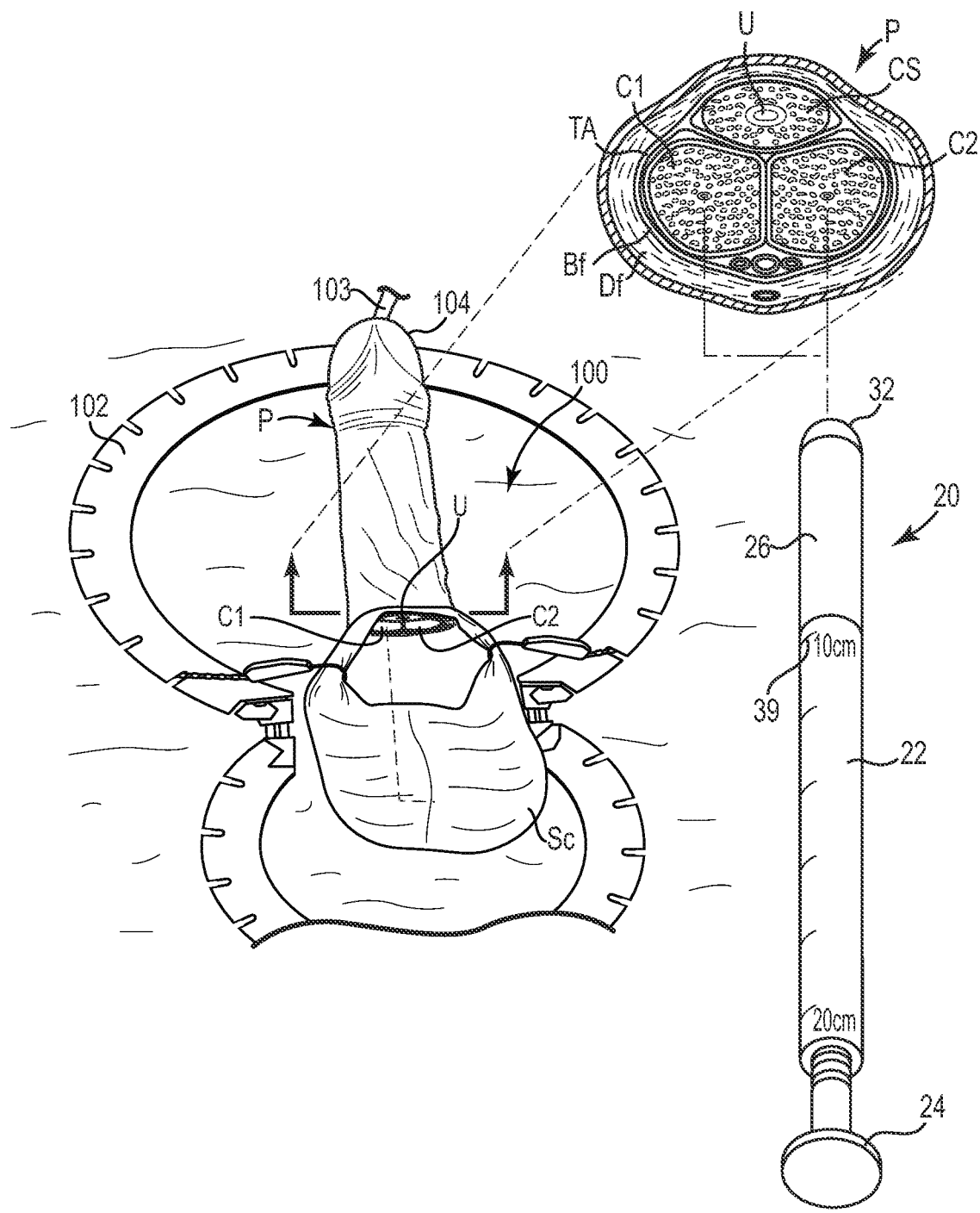
FIG. 5B is a schematic view of the primed instrument illustrated in FIG. 5A in a configuration to measure a corpora cavernosa of a patient.
Figure 5C:
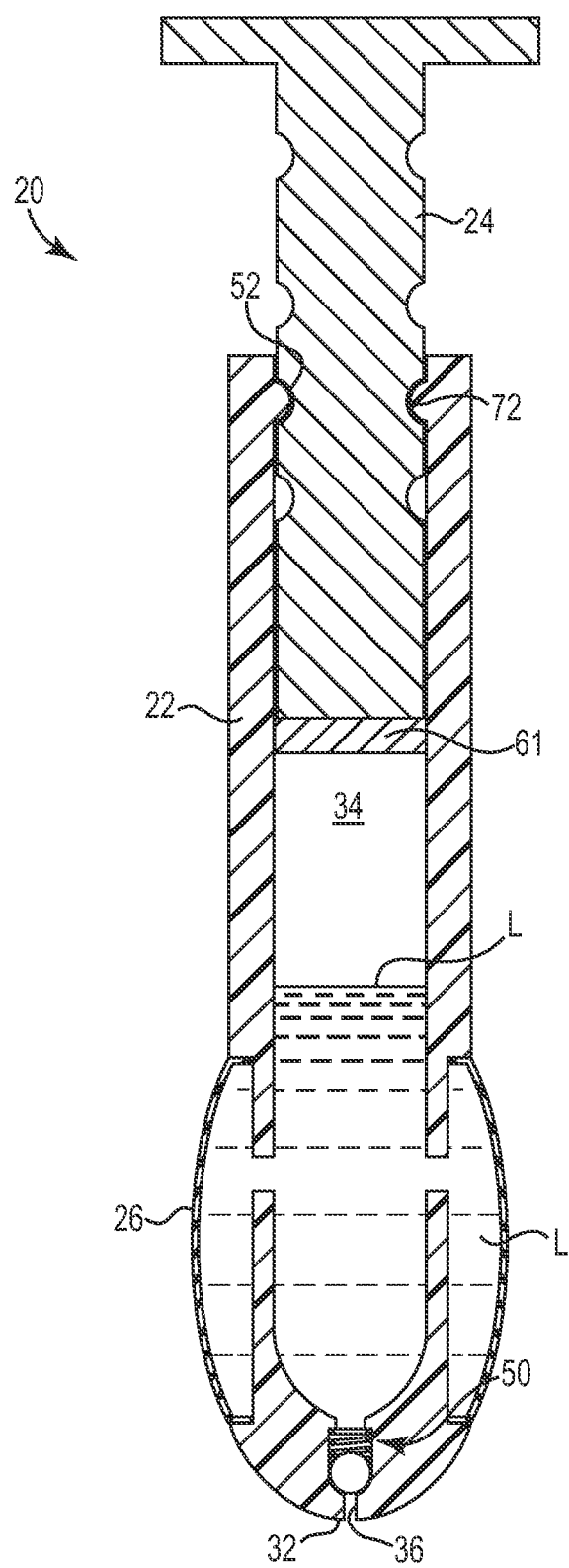
FIG. 5C is a cross-sectional view of one embodiment of the liquid within the fluid chamber pressurized by the plunger to dilate the distal end portion of the instrument for dilating the corpora cavernosa of the patient prior to implantation of the penile implant.

FIGS. 5A, 5B, and 5C are views, respectively, of the instrument 20 primed by aspirating liquid into the fluid chamber 34, the primed instrument 20 ready to measure a corpora cavernosa of a patient, and the expandable member 26 dilated outward to provide the instrument 20 with an increased outside diameter for dilating the corpora cavernosa of the patient.

FIG. 5A is a cross-sectional view of one embodiment of the instrument 20 primed by aspirating liquid L into the internal fluid chamber 34. In one exemplary approach, the surgeon (or a surgical assistant) presses the plunger 24 into the shaft 22 (as shown in FIG. 1) and dips the distal end 32 into a tray or container 90 of liquid L. The plunger 24 has been retracted proximally (e.g., the handle 56 has been moved away from the shaft 22) to reduce the pressure inside of the fluid chamber 34 and aspirate the liquid L from the container 90 into the fluid chamber 34. The seal 61 contributes to maintaining the low suctioned pressure within the fluid chamber 34 that allows the instrument 20 to draw the liquid L from the container 90 into the chamber 34.

In one embodiment, the plunger 24 is retracted proximally relative to the shaft 22 until the distal-most stop detent 72 is engaged with the detent 52 to maximize the volume of the fluid chamber 34. The check valve 50 allows the liquid L in the container 90 to flow into the orifice 36 and into the fluid chamber 34, but prevents the liquid L within the fluid chamber 34 from exiting the orifice 36. In one embodiment, the relatively low pressure within the fluid chamber 34 as the liquid L is drawn from the container 90 will draw the expandable member 26 inward toward the shaft 22, which provides an even more compact profile for the instrument 20 that contributes to the ease of insertion of the shaft 22 into one of the corpora cavernosum areas of the patient.

FIG. 5B shows a patient prepped and ready to have the corpora cavernosa C1 and C2 of the penis P measured and subsequently dilated by the instrument 20 prior to implantation of a penile prosthetic. While the penile prosthetic is not shown, it would typically include a pair of inflatable cylinders, a reservoir, and a pump employed to transfer fluid to/from the reservoir.

The fluid chamber 34 (FIG. 5A) has been primed with the liquid L. The expandable member 26 of the instrument 20 is in a deflated state (or a non-inflated state) such that the shaft 22 is rigid and has a uniformly smooth outside diameter suited for measuring a length of one of the corpora cavernosa C1 or C2. The instrument 20 is employed by inserting the rigid shaft 22 into the corpora of the penis to first measure the corpora C1 and C2 with the expandable member 26 not inflated. After the lengths of the corpora C1 and C2 are records the expandable member 26 is dilated to core tissue from the corpora C1 and C2. For example, while the instrument 20 is inserted into one of the corpora cavernosum, the expandable member 26 is expanded to subsequently dilate the corpora for insertion of the cylinders.

The groin area 100 of the patient is shaved, cleaned and suitably prepped with a surgical solution prior to draping with a sterile drape as directed by the healthcare provider's procedures. A retraction device, such as a retractor 102 sold under the trademark Lone Star and available from Lone Star Medical Products of Stafford, Tex., is placed around the penis P if so desired by the surgeon to establish a surgically clean field. A catheter 103 is inserted into the urethra U from the distal end 104 of the penis P.

Thereafter, the surgeon forms an incision to access the corpora cavernosa C1 and C2 of the penis. One suitable incision includes the transverse scrotal approach, where the surgeon forms a 2-3 cm transverse incision through the subcutaneous tissue of the median raphe of the upper scrotum Sc and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed to allow the surgeon to access and subsequently dilate the corpora cavernosa C1 and C2.

The penis P is reclined against the torso such that the urethra U, surrounded by corpus spongiosum tissue, is oriented upward. The instrument 20 provides a substantially uniform outside diameter that is configured to slide into the corpora and allow the shaft 22 to measure the length of each of the corpora cavernosum (C1 or C2). In the corpora measurement configuration illustrated in FIG. 5B, the entire length of the shaft 22 is uniformly unobstructed and suited for easy insertion into each corpora cavernosum.

The surgeon typically will insert a blunt-ended scissors or other elongated tool to separate a portion of the spongiosum material to open a pathway for the instrument 20. The surgeon inserts the shaft 22 into the corpora cavernosa C1 and C2 to measure the proximal and distal length of each corpora cavernosum C1 and C2. For example, the shaft 22 is inserted into one of the corpora cavernosa C1 or C2 forward in the distal penis toward the glans penis, the distal measurement is recorded by reading the indicia 39, and the shaft 22 is inserted into the same corpora cavernosa C1 or C2 rearward in the proximal penis toward the crus, of the penis to record the proximal length of the corpora by reading the indicia 39. The distal and proximal measurements would typically be made in reference to a "stay stitch" temporarily placed in the incision. The sum of the distal and the proximal measurements represent the length of the corpora into which the implant is placed. This procedure is repeated for the other of the corpora cavernosa C1 or C2 to measure the length of the companion corpora.

Thereafter, each corpora cavernosum C1 and C2 is dilated distally and proximally with the instrument 20. One exemplary method of preparing an opening formed in the penis P for reception of a penile prosthetic includes aspirating a fluid through the orifice 38 formed in the distal end 32 of the shaft 22; measuring a length of the opening in the corpora of the penis with the shaft 22; expanding, with the fluid, the balloon 26 that is attached to the shaft; and dilating a diameter of the opening formed in the penis with the expanded balloon. In one embodiment, the instrument 20 is employed to first measure the length of each corpora cavernosum C1 and C2, and while the instrument is still inserted into one of the corpora cavernosum C1 and C2, the expandable member 26 is dilated to a first expanded diameter in a controlled manner through the use of the detent 52 and the stop detents 72, the corpora cavernosum is dilated to the first diameter, and then the expandable member 26 is dilated to a second larger expanded diameter by indexing to the next stop detent 72, where the corpora cavernosum is dilated to the second diameter.

FIG. 5C illustrates the instrument 20 with the expandable member 26 pressurized by the liquid L and dilated to a diameter that is larger than the diameter D1 of the shaft 22 (see FIG. 4B). The check valve 50 prevents the liquid L from exiting the orifice 36 at the distal end 32 of the shaft 22 as the plunger 24 pressurizes the liquid L. The expanded distal end portion 42 of the instrument 20 is inserted first proximally and then distally into one of the corpora C1 or C2 to dilate the corpora to the expanded diameter provided by expandable member 26. In a like manner, the surgeon would insert the distal end 32 of the instrument 20 first proximally and then distally into the other of the corpora C1 or C2 to dilate the other corpora to the diameter of the expanded member 26 of instrument 20.

The instrument 20 is configured to provide the surgeon with the option of first dilating the corpora to the diameter D1 of the shaft 22 (FIG. 4B), incrementally advancing the plunger 24 into the shaft 22 to expand the expandable member 26 to dilate the corpora to a diameter D2, and again incrementally advancing the plunger 24 into the shaft 22 to expand the expandable member 26 to dilate the corpora to a diameter D3.

In one embodiment, the plunger 24 is advanced into the shaft 22 until a first one of the stop detents 72 engages with the detent 52 and the expandable member 26 inflates from the diameter D1 of the shaft 22 to a second diameter that is approximately 125% of the diameter D1, after which the surgeon dilates the corpora to approximately the second diameter; the plunger 24 is incrementally advanced into the shaft 22 until a next one of the stop detents 72 engages with the detent 52 and the expandable member 26 further inflates to a third diameter that is approximately 150% of the diameter D1, after which the surgeon dilates the corpora to approximately the third diameter; and the plunger 24 is incrementally advanced into the shaft 22 until a next one of the stop detents 72 engages with the detent 52 and the expandable member 26 further inflates to a fourth diameter that is approximately 150% of the diameter D1, after which the surgeon dilates the corpora to approximately the fourth diameter. In one embodiment, the instrument 20 is beneficially configured such that the first end or is about 8 mm, the second diameter is about 10 mm, the third diameter is about 12 mm, and the fourth diameter is about 14 mm, although any suitable range of from D1 of about 2 mm to D4 of about 20 mm is acceptable.

In one embodiment, the plunger 24 is retracted proximally relative to the shaft 22 to deflate the balloon/expandable member 26 to the diameter of D1 as the surgeon transitions between dilating the corpora between the second diameter, the third diameter, and the fourth diameter.

After dilation of the corpora cavernosum C1 and C2, the surgeon selects a proper length of implant and proceeds with placement of cylinders of the implant within the fully dilated corpora.

Embodiments provide an instrument that is configured to prepare a penis for implantation of a penile prosthetic, where the instrument includes a shaft suited for measuring a length of the corpora cavernosum and a plunger that is movable relative to the shaft to inflate an expandable member away from the shaft, thus widening the shaft in a manner that will dilate the corpora cavernosum. Thus, a single instrument is provided that has improved cost effectiveness and procedural efficiency over the prior tools, and is suited to measure and dilate the corpora cavernosum of the penis.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An instrument configured to prepare a penis for implantation of a penile prosthetic, the instrument comprising:
   a shaft extending between a distal end and a proximal end of the instrument, a fluid chamber formed inside the shaft, the distal end of the instrument including an orifice through which fluid is drawn from outside the instrument into the fluid chamber;
   a plunger movably inserted into the shaft;
   an expandable member sealed to a distal end portion of the shaft; and
   a fluid pathway formed in the shaft communicating between the fluid chamber and the expandable member;
   wherein the plunger is movable to inflate the expandable member away from the shaft.

2. The instrument of claim 1, wherein the fluid chamber is formed as an axial bore within the shaft.

3. The instrument of claim 2, wherein the plunger is movably inserted into the fluid chamber via the proximal end of the shaft and comprises a rod having a seal that contacts the axial bore.

4. The instrument of claim 1, wherein the distal end portion of the shaft includes a check valve located proximal the orifice, the check valve configured to prevent the fluid in the fluid chamber from exiting the distal end of the shaft.

5. The instrument of claim 1, wherein an exterior surface of the distal end portion of the shaft includes a recessed shoulder, the expandable member sealed to the recessed shoulder.

6. The instrument of claim 1, wherein the expandable member is sealed around a periphery of the distal end portion of the shaft.

7. The instrument of claim 6, wherein the distal end portion of the shaft is recessed relative to a proximal end portion of the shaft.

8. The instrument of claim 7, wherein the expandable member is disposed in the recessed distal end portion of the shaft.

9. The instrument of claim 8, wherein the expandable member configures the shaft to provide a substantially uniform diameter between the proximal and distal end portions when the expandable member in its deflated state.

10. The instrument of claim 1, wherein the shaft has a shaft diameter and the expandable member is inflatable from a first diameter approximately equal to the shaft diameter to a second diameter that is approximately 125% of the shaft diameter.

11. The instrument of claim 10, wherein the expandable member is inflatable to a second diameter that is approximately 150% of the shaft diameter.

12. The instrument of claim 10, wherein the expandable member is inflatable to a second diameter that is approximately 200% of the shaft diameter.

13. The instrument of claim 1, wherein the plunger is movable longitudinally relative to the shaft and the expandable member is movable laterally relative to the shaft.

* * * * *